(12) United States Patent
Deuar

(10) Patent No.: US 6,647,801 B1
(45) Date of Patent: Nov. 18, 2003

(54) METHOD, APPARATUS AND SUPPORT FOR TESTING POLES

(75) Inventor: Krzysztof Jan Deuar, Morayfield (AU)

(73) Assignee: Anna Teresa Deuar, Morayfield (AU)

( * ) Notice: Subject to any disclaimer, the term of this patent is extended or adjusted under 35 U.S.C. 154(b) by 0 days.

(21) Appl. No.: 09/744,964

(22) PCT Filed: Aug. 13, 1999

(86) PCT No.: PCT/AU99/00661

§ 371 (c)(1),
(2), (4) Date: Feb. 13, 2001

(87) PCT Pub. No.: WO00/09986

PCT Pub. Date: Feb. 24, 2000

(30) Foreign Application Priority Data

| Aug. 13, 1998 | (AU) | PP 5217 |
| Mar. 18, 1999 | (AU) | PP 9261 |
| May 6, 1999 | (AU) | 26947/99 |

(51) Int. Cl.$^7$ .................. G01N 11/00; G01N 19/00; B66F 7/20; G01L 1/00
(52) U.S. Cl. .................. 73/823; 73/806; 254/30; 702/43
(58) Field of Search .......... 73/823, 825, 816, 73/806, 786, 849; 702/43; 254/30

(56) References Cited

U.S. PATENT DOCUMENTS

| 2,176,530 A | * | 10/1939 | Greulich | 52/170 |
| 2,854,847 A | * | 10/1958 | Brady | 73/786 |
| 3,320,714 A | * | 5/1967 | Barrett | 173/112 |
| 3,350,822 A | | 11/1967 | Nachazel | |
| 3,738,072 A | * | 6/1973 | Adrian | 52/170 |
| 3,773,292 A | * | 11/1973 | Thiermann | 254/30 |
| 4,516,365 A | * | 5/1985 | Chapman | 52/170 |
| 4,697,396 A | | 10/1987 | Knight | |
| 4,987,718 A | * | 1/1991 | Knight | 52/170 |
| 5,051,919 A | * | 9/1991 | Deuar | 702/43 |
| 5,212,654 A | * | 5/1993 | Deuar | 702/43 |
| 5,383,749 A | * | 1/1995 | Reisdorff et al. | 405/231 |

FOREIGN PATENT DOCUMENTS

| AU | B-71869/87 | 8/1987 |
| AU | A-39091/89 | 7/1989 |
| DE | 819575 | 11/1951 |

* cited by examiner

Primary Examiner—Edward Lefkowitz
Assistant Examiner—Lilybett Martir
(74) Attorney, Agent, or Firm—Hoffman, Wasson & Gitler

(57) ABSTRACT

A pole support for ground poles, such as telephone poles and power poles, is disclosed. The support can be driven into the ground next to the pole. It has a pair of spaced apart longitudinal end plates which are interconnected intermediate their ends by an intermediate plate. The end plates are spaced apart to allow the ground pole to pass at least partially between the end plates. Each end plate has a front longitudinal edge which, in use, is adjacent to the pole and a rear longitudinal edge which, in use, is directed away from the pole. The pole support has means to reduce sharp edges on the rear longitudinal edges. Also disclosed is a method for testing pole strength which comprises applying a load to the pole and either measuring its displacement or observing if it withstands the load. The amount of load applied to the pole and the degree of displacement is undergoes can be used to calculate the residual strength of the pole.

25 Claims, 8 Drawing Sheets

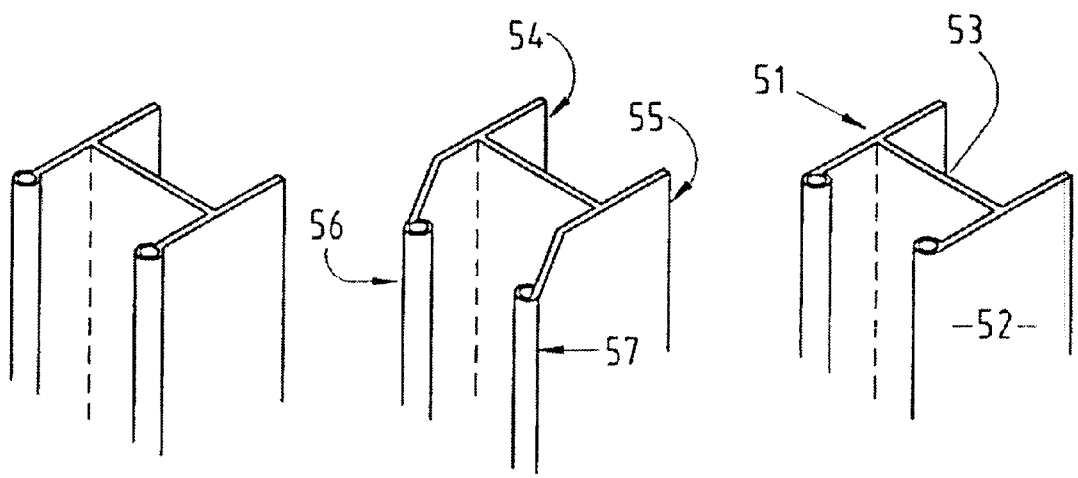
FIG 8.    FIG 7B.    FIG 7A.
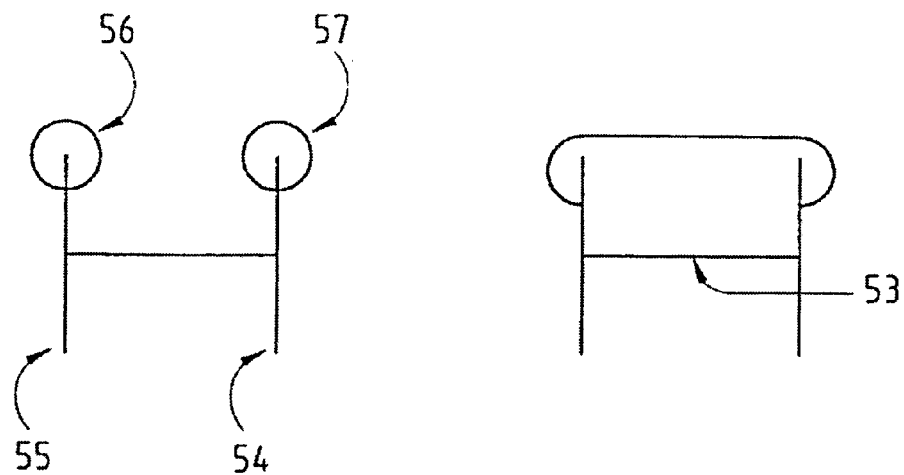
FIG 9.    FIG 10.
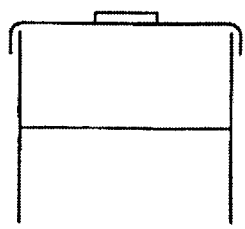 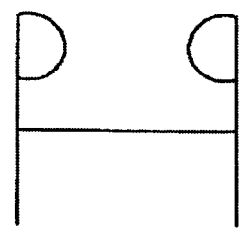
FIG 11.    FIG 12.

US 6,647,801 B1

METHOD, APPARATUS AND SUPPORT FOR TESTING POLES

FIELD OF THE INVENTION

This invention relates to a method of and apparatus for the testing of poles. Throughout the specification, the term "poles" shall be used to include electricity, telephone and telegraphic poles; fence and retaining wall posts and the like.

This invention also relates to a pole support for ground poles and particularly relates to a pole support which can be driven into the ground next to a ground pole to support the pole against leaning or toppling over.

BACKGROUND ART

Power poles and telephone poles are conventionally formed from wood, steel or concrete and are pounded into the ground, or a hole is drilled into the ground and the pole is inserted into the hole.

Once the pole has been put into the ground, the upper part of the pole is arranged to receive power cables, data cables, telephone cables and the like. For some poles, the weight of these cables can be quite considerable and some poles contain additional devices such as power transformers which are quite heavy.

Occasionally, the poles need to be supported to an extent greater than that provided to the pole merely by being driven into the ground. It is known to provide additional support by driving a profiled steel member into the ground next to the pole and by bolting the pole to the profiled steel member.

As the pole can exert considerable force against the steel member, the steel member has required a complicated profile in order to prevent buckling under the force of the pole.

A disadvantage with these types of pole supports is that the required profile is complex and makes the supports expensive to manufacture. Also, existing profiles are not entirely satisfactory in their supporting ability.

Another reason for the complicated profile in existing pole supports is to reduce or eliminate sharp edges which can cause injury to Pole supports are also required as a precaution when the strength of the pole is tested. One method for testing poles in the ground is to apply a load to the pole. A pole support is desirable to support the pole in case it breaks under test conditions.

Wood rot, bores, termites and other factors operate to reduce the strength, and therefore, the service life of poles. For safety reasons, the strength of the poles must be periodically checked and the future life of the poles established. As wood rot generally occurs below the ground level, a simple visual inspection is not sufficient and mechanical strength tests must be carried out.

To date, no simple, efficient and reliable test method has been available so poles are often replaced well before the end of their effective life. This naturally increases the operating expenses of the electricity authority.

OBJECT OF THE INVENTION

It is an object to provide at least one simple method for testing poles.

It is a preferred object to provide an apparatus suitable for the method.

In one form, the invention resides in a method for testing a pole including the steps of:

calculating the minimum required strength of the pole and load to be applied to the pole equivalent to the minimum strength including any required safety factors, applying a preset load to the pole equivalent to the calculated minimum strength, and observing if the pole withstands the applied load without failure and so meets the minimum required strength.

In a second form, the invention resides in an apparatus for testing a pole including:

means to calculate the minimum required strength of the pole and load to be applied to the pole equivalent to the minimum strength, means to apply a load to the pole, means to measure the load applied to the pole, and (a) means to calculate the residual strength of the pole from the applied load, or (b) means to measure the displacement of the pole under the applied load, means to calculate the residual strength of the pole from the applied load and the displacement, and means to detect the pole failure.

In a third form, the invention resides in a method for testing the residual strength of a pole including the steps of:

applying a preset load to the pole, measuring the displacement of the pole under the load, and from the applied load and the displacement, calculating the residual strength of the pole from predetermined formula(e), tabulated scales, or by a programmed calculator or computer.

In a fourth form, the invention relates to a method for testing the residual strength of a pole including the steps of:

applying a load to the pole to cause the pole to undergo a preset displacement, measuring the load applied to the pole, and from the applied load and the displacement, calculating the residual strength of the pole from predetermined formula(e), tabulated scales, or by a programmed calculator or computer.

The minimum required strength of the tested pole and equivalent load to be applied to the pole may be calculated by a hand-held or desk top computer or predetermined from a formula(e) or table.

The load may be applied by pushing and/or pulling the pole at any height above the ground level and may be effected by a mechanical jack or turnbuckle, hydraulic or pneumatic ram, a winch or other suitable mechanical, hydraulic or electrical means which may be portable, mounted on wheels or vehicles.

The applied load is preferably measured by a load cell or other suitable equivalent means.

The applied loads and other test data as well as pole test results may be recorded manually or automatically by the use of any suitable computer system.

The displacement of the pole is preferably measured by displacement gauges, strain gauges or the like mounted on a reference frame.

The pole failure may be detected by a predetermined value of pressure drop on pressure gauges, noise level in acoustic devices, or by any other suitable means.

Stability of the pole in case of its failure can be provided by a safety frame or safety rope or pole buoy or safety clamps mounted to the boom of the crane of the pole testing vehicle or other heavy equipment.

The excessive movement of the pole is limited by a chain, rope, frame, pole buoy, bar, or clamps connected to the pole testing equipment or other heavy and stable machinery and objects such as concrete blocks, adjacent trees or the like.

The present invention is also directed to a pole support which may overcome the abovementioned disadvantages or provide the public With a useful or commercial choice.

In another form, the invention resides in a pole support for ground poles and which can be driven into the ground next to the pole, the support having a pair of spaced apart longitudinal end plates which are interconnected intermediate their ends by an intermediate plate, the end plates being spaced apart to allow the ground pole to pass at least partially between the end plates, each end plate having a front longitudinal edge which in use is adjacent the pole and a rear longitudinal edge which in use is directed away from the pole, the pole support having means to reduce sharp edge on the rear longitudinal edge.

In another form, the invention resides in a pole support for ground poles and which can be driven into the ground next to the pole, the support having a pair of spaced apart longitudinal end plates which are interconnected intermediate their ends by an intermediate plate, the end plates being spaced apart to allow the ground pole to pass at least partially between the end plates, each end plate having a front longitudinal edge which in use is adjacent the pole and a rear longitudinal edge which in use is directed away from the pole.

The pole support has a much simpler profile which still allows good support to the ground pole.

The pole support can be formed from steel plate or other material which is strong enough to be driven into the ground and to support the pole. The size, thickness and length of the pole support can vary depending on the forces exerted on the support, and the size and type of the pole.

The spaced apart longitudinal end plates are preferably substantially parallel to each other and are suitably sufficiently long to allow them to be driven into the ground to a suitable distance while still providing sufficient. length above the ground to provide support to the ground hole. This again can vary to suit, but lengths of 2 to 5 m are envisaged.

The width of the longitudinal end plates can vary depending on the degree of support required and the size of the pole. For instance, increasing the width of the end plates will increase the stiffness of the pole support and therefore the ability of the support to withstand forces applied to it. Increasing the thickness of the end plates will also achieve a similar result.

For manufacturing and transportation reasons, the end plates should not be excessively wide, but the plates should have sufficient width to allow the support to be hammered into the ground using the upper edge of the end plates (and possibly the intermediate plate) as a hammering surface.

The spacing between the end plates will vary depending on the diameter or cross-sectional size of the pole. As most power poles are between to 50 cm in diameter, it is preferred that the end plates are similarly spaced apart such that the ground pole can pass at least partially between the end plates. For reasons of safety, it is preferred that there is minimal gap between the end plate and the outer surface of the pole which could snag fingers of passers by or become a collection point for dirt and debris which may reduce the effective life of the pole.

The spacing between the end plates can be determined by the width of the intermediate plate. It is preferred that the end plates and the intermediate plates are all formed from the same material which is suitably steel, and that the plates are integrally formed together, or welded together to form a strong rigid structural unit which can be driven into the ground without falling apart. The intermediate plate preferably extends entirely along the length of the pole support by which is meant that the intermediate plates and the end plates are all of the same length.

Each end plate and the intermediate plate is preferably substantially rectangular when viewed in plan. Each end plate has a front longitudinal edge and an opposed rear longitudinal edge. The front longitudinal edge is defined as the edge which extends towards the pole, while the rear longitudinal edge is the other edge.

For reasons of strength and improved use, it is preferred that the end plates are plate-like which present longitudinal edges which are approximately at right angles and therefore present a quite sharp hard steel edge which can cause injury.

For this reason, another form of the invention includes a means by which the sharp edge can be eliminated or at least reduced to provide a pole support having suitable safety characteristics.

In one form, this can be achieved by providing a curved portion on or adjacent the rear longitudinal edge of each end plate. The curved portion can be formed by bending the longitudinal edge inwardly. Alternatively, a separate curved portion can be attached by suitable means to the rear longitudinal edge, for instance by spot, welding. In a further alternative, the means can include a rod or tube which is attached by any suitable means to the rear longitudinal edge to eliminate or at least partially reduce the sharp edge. In a further alternative, a cover plate or cover member can be positioned over one or both of the rear longitudinal edges to remove the sharp edge.

BRIEF DESCRIPTION OF THE DRAWINGS

Embodiments of the invention will be described with reference to the following drawings in which

FIGS. 7A and 7B illustrate a first and second variation of an embodiment of the invention.

FIG. 8 illustrates a second embodiment of the invention.

FIG. 9 illustrates a third embodiment of the invention.

FIG. 10 illustrates a fourth embodiment of the invention.

FIG. 11 illustrates a fifth embodiment of the invention.

FIG. 12 illustrates a sixth embodiment of the invention.

BEST MODE

Figure 1:
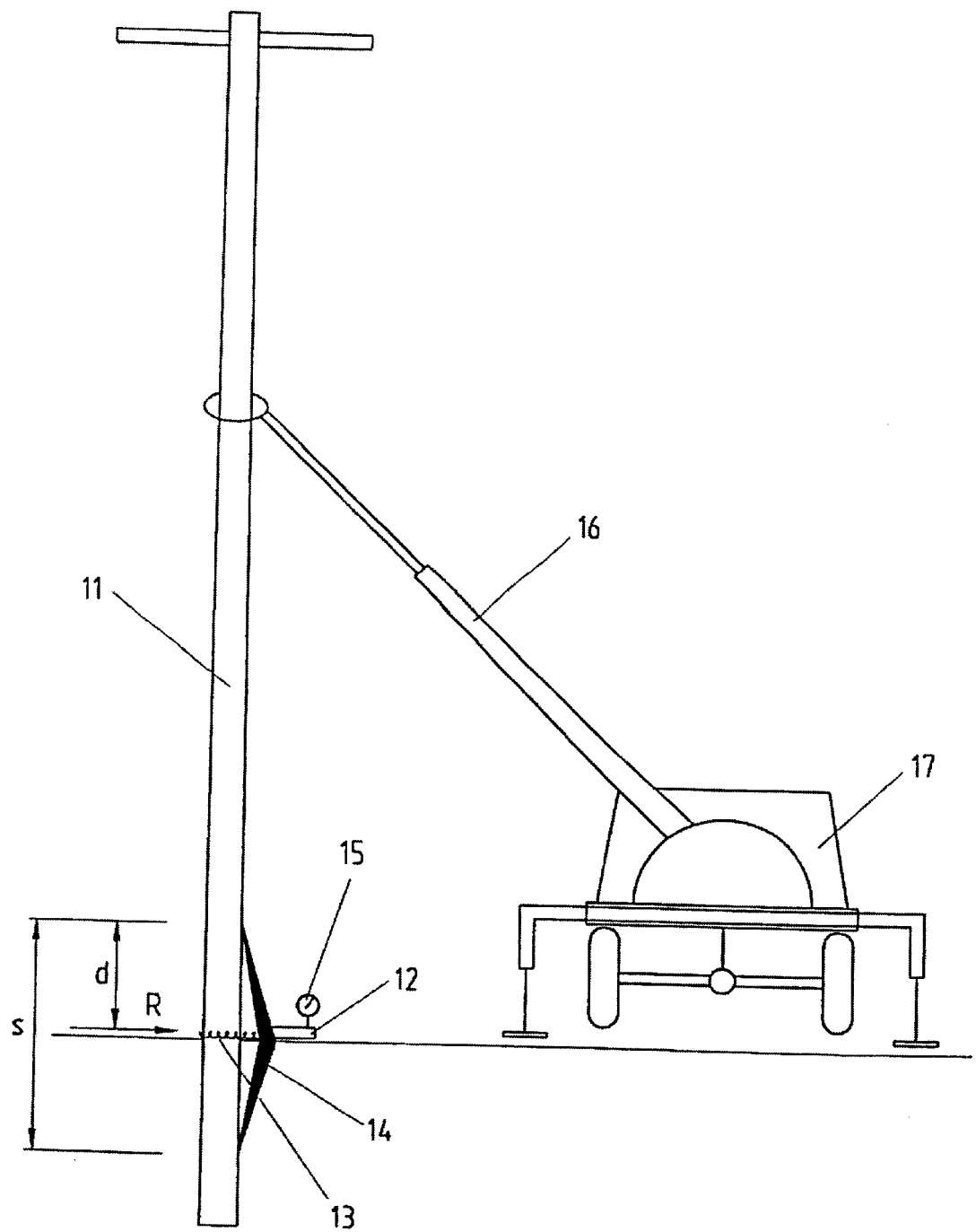
FIGS. 1 to 6C are schematic views showing a pole being tested with a specially designed apparatus.

Referring to FIG. 1, a pole 11 is pulled with a hydraulic ram 12 through a chain 13 and simultaneously pushed with the ends of a beam 14 until a preset load R is obtained on a load cell 15.

The beam 14 can be operated by a crane boom 16 mounted on a truck 17.

Having the values of the predetermined required strength of pole M, the span s of the beam 14 and the distance d between the hydraulic ram 12 and one of the ends of the beam, the load R to be obtained on the load cell can be easily calculated from the following formula:

$$R = \frac{M}{d} \frac{s}{s-d}$$

Stability of the pole in case of its failure is provided by a safety boom 16 of a truck 17, or by a pole support illustrated in FIGS. 7 to 15.

Figure 2:
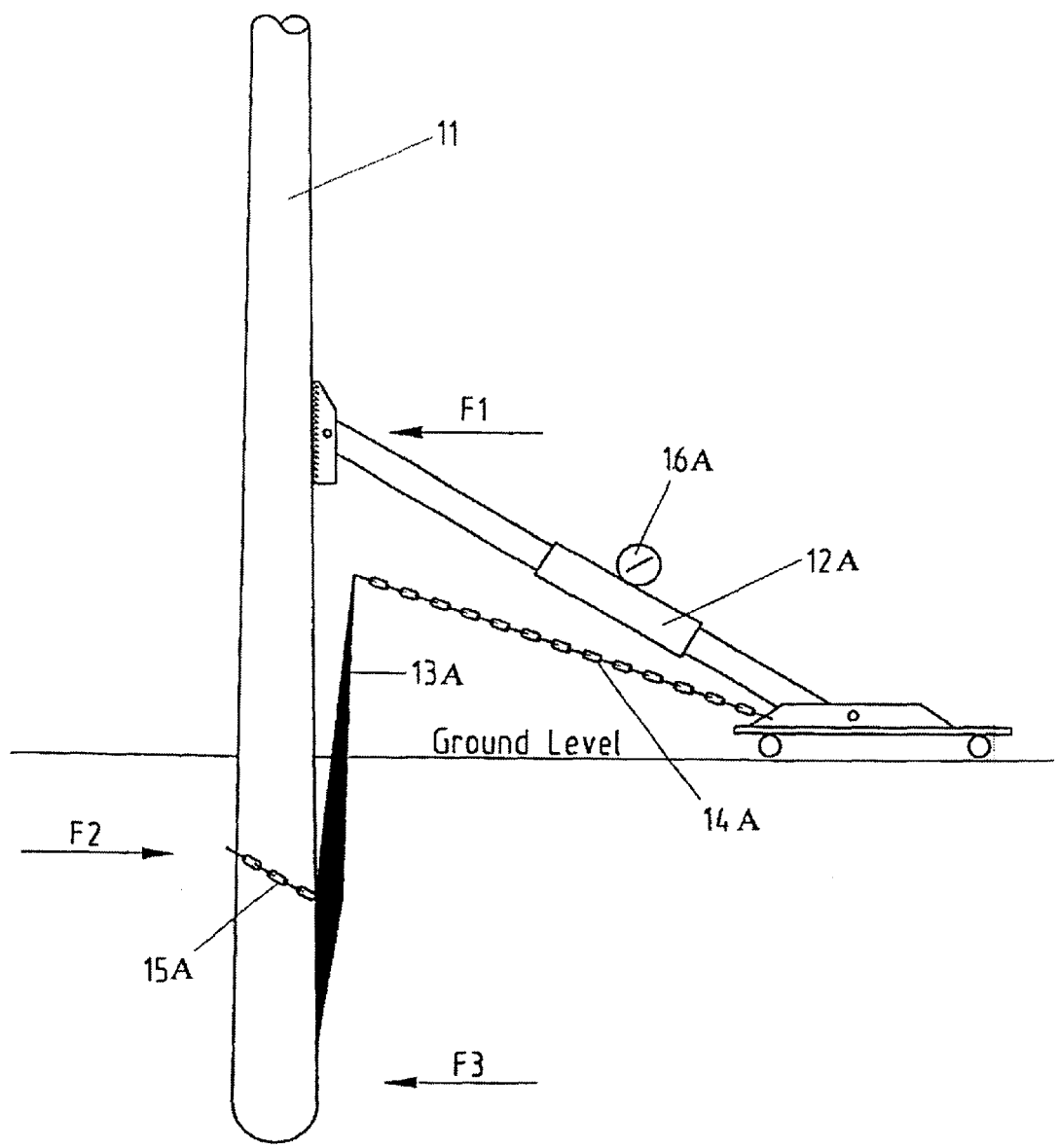

Referring to FIG. 2, a pole 11 is simultaneously:

pushed with a hydraulic ram 12 which by its extension pulls the top end of a vertical beam 13 through a chain 14, and pulled with a chain which is attached to the lower part of the vertical beam 13, and pushed with the bottom end of the vertical beam 13 below the ground level.

The length of the chain 14 can be adjusted by a winch or additional hydraulic ram or the like so that a ratio between forces F1, F2, and F3 (where forces F2 and F3 are usually much greater than force F1) can be changed. The idea is to obtain such a ratio between forces F1, F2, and F3 that the pole is bent at the ground level yet it does not deflect at its top and therefore there is no need of slackening or disconnecting of the wires attached to the pole top.

The apparatus shown of FIG. 2 can be portable, on its own wheels or operated by a truck mounted crane or the like.

Having the values of the predetermined required strength of the pole, the target pressure on a load cell 16 or the like can be easily determined.

Figure 3:
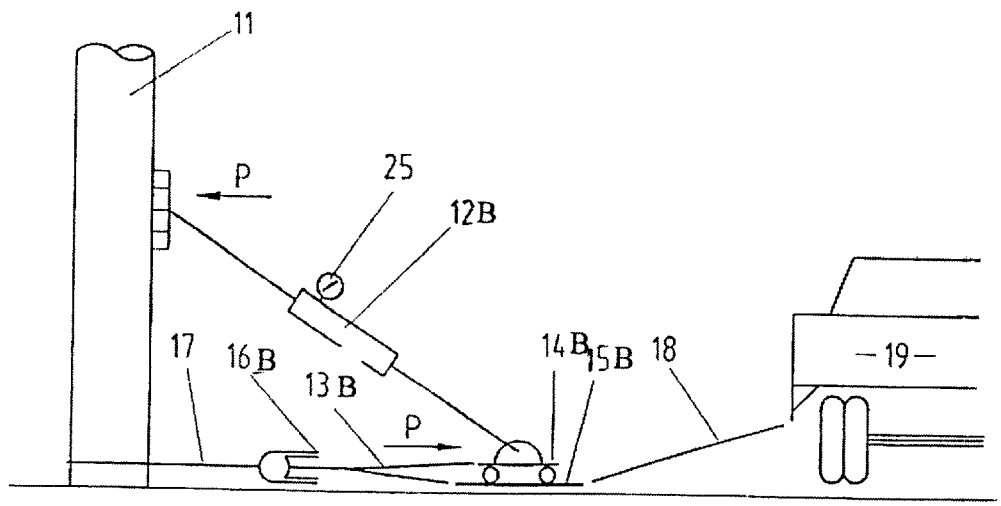
Figure 4:
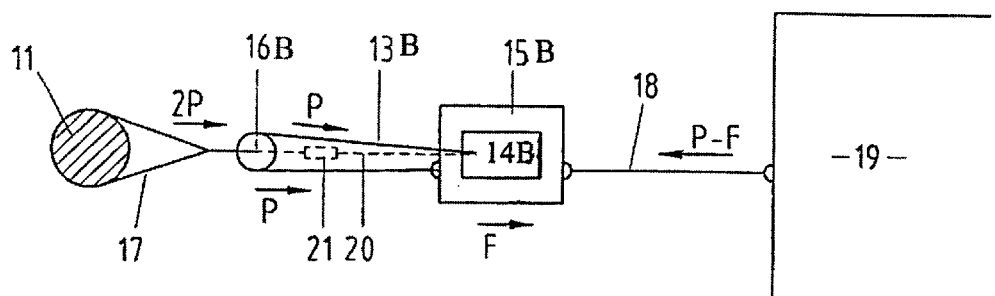

Referring to FIGS. 3 and 4, a pole 11 is simultaneously:

pushed with a hydraulic ram 12 which by is extension applies tension force P to a chain 13 via a foot plate 14 travelling freely on top of a plate which is pushed to the ground with a vertical component of force exerted by the hydraulic ram 12, and pulled with force 2P produced by the chain 13 via a pulley 16 and chain 1; chain 13 runs from the foot plate 14 around the pulley 16 to the plate 15; if friction force F between the plate and ground surface is less than tension force P in the chain 13 then the difference P−F is taken by a chain 18 attached between the plate and a vehicle 19.

The pulling force applied to the pole 11 at the ground line can be adjusted in the range between P and 2P by an additional chain 20, running from the foot plate 14 to the pulley 16, which is tightened by a pulling ram or chain puller 21.

Figure 5:
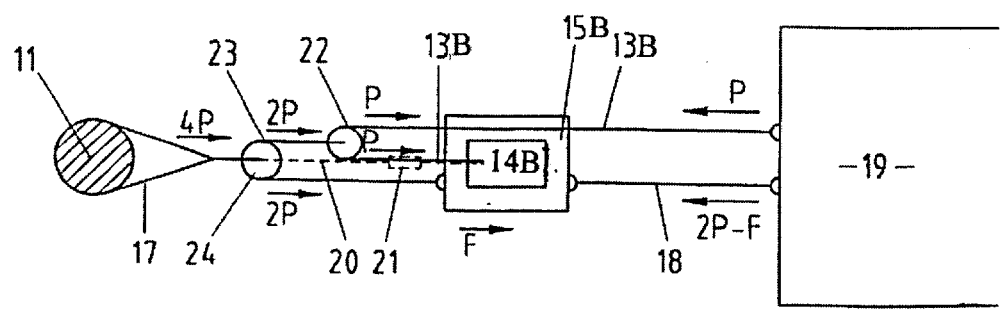

Referring to FIGS. 3 and 5, a pole 11 is simultaneously:

pushed with a hydraulic ram 12 which by its extension applies tension force P to a chain 13 via a foot plate 14 travelling freely on top of a plate which is pushed to the ground with a vertical component of force exerted by the hydraulic ram 12, and pulled with force 4P produced by the chain 13 via a pulley 22, chain 23, pulley 24, and chain 17; chain 13 runs from the foot plate 14 around the pulley 22 to a vehicle 19; chain 23 runs from the pulley 22 around the pulley 24 to the plate 15; if friction force F between the plate and ground surface is less than tension force 2P in the chain 23 then the difference 2P−F is taken by a chain 18 attached between the plate and vehicle 19.

The pulling force applied to the pole 11 at the ground line can be adjusted in the range between P and 4P by an additional chain 20, running from the foot plate 14 to the pulley 24, which is tightened by a pulling ram or chain puller 21.

The idea is to increase the force pulling the pole at the ground line to such a magnitude that the pole is bent at the ground level yet it does not deflect at its tope and therefore there is no need of slackening or disconnecting of the wires attached to the pole top.

The apparatus shown in FIGS. 3, 4 and can be portable, on its own wheels or operated by a truck mounted crane or the like.

Having the values of the predetermined required strength of the pole, the target pressure on a load cell or the like can be easily determined.

Figure 6A:
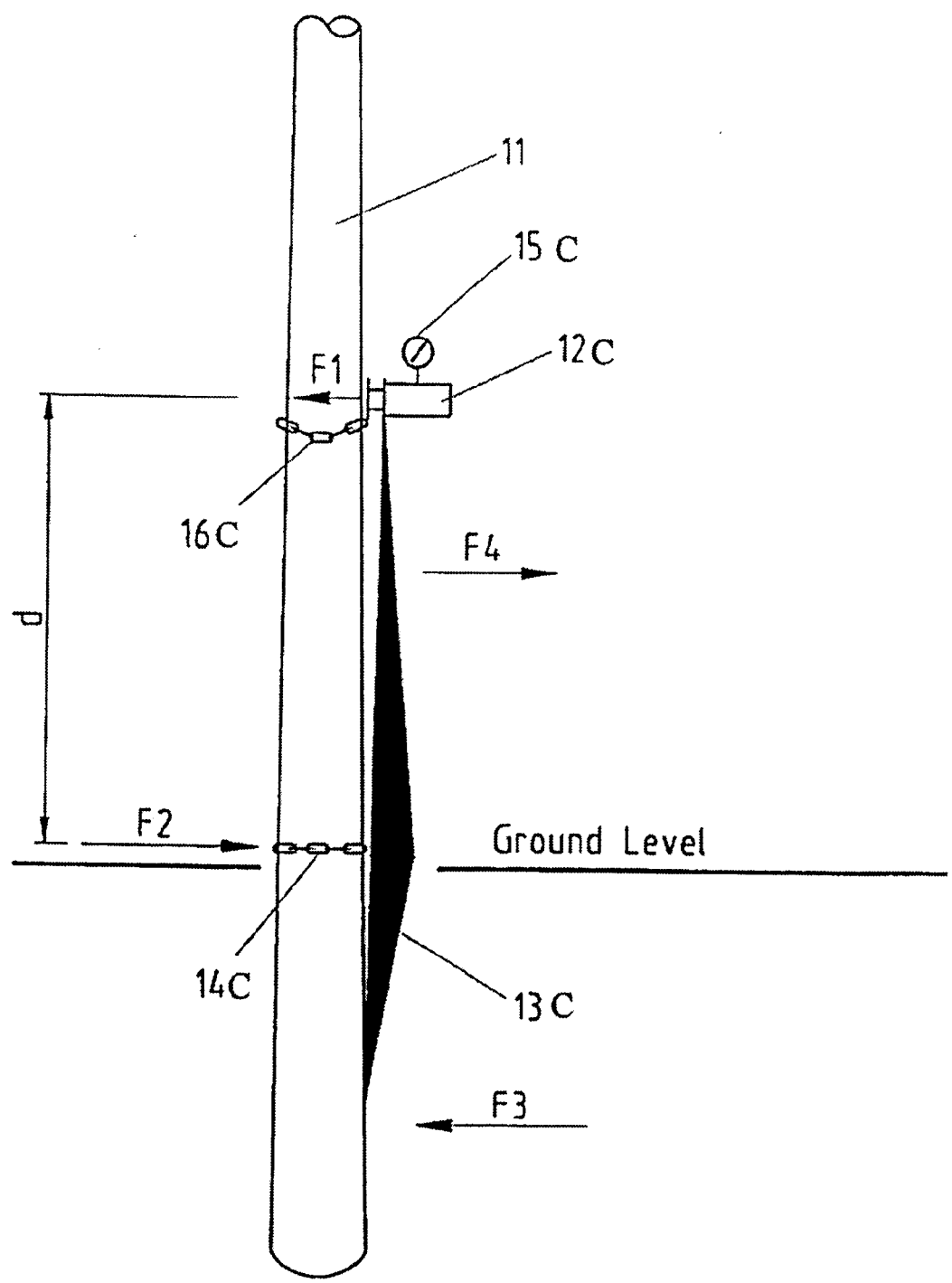

Referring to FIG. 6A, a pole 11 is simultaneously:

pushed with force F1 by means of a hydraulic ram 12 which at the same time, by its extension, pushes the top end of a vertical beam 13 away from the pole 11, and pulled with force F2 by means of a chain 14 which is attached to the lower part of the vertical beam 13, and pushed with force F3 at the bottom end of the vertical beam 13 below the ground level, until a preset load F1 is obtained on a load cell 15.

The beam 13 can be operated manually or by suitable mechanical means such as a crane, hammer, or the like.

The beam 13 may be additionally loaded with force F4 by suitable mechanical means such as a crane, hydraulic ram, or the like so that the pole 11 is bent at the ground level yet it does not move at its top and therefore there is no need of slackening or disconnecting of the wires attached to the pole top.

A chain 16 is attached to the head of the hydraulic ram 12 for safety purpose in case of the pole failure.

The apparatus shown in FIG. 6A can be portable, on its own wheels or operated by a truck mounted crane or the like.

Having the values of the predetermined required bending strength of the pole M and the distance d between the hydraulic ram 12 and the chain 14, the target force F1 to be obtained on the load cell can be easily calculated from the following formula:

$$F1 = M/d$$

Stability of the pole in case of its failure is provided by a combination of the stake 13 embedded in the ground and safety chain 16 connected to the stake 13 through the hydraulic ram 12.

Figure 6B:
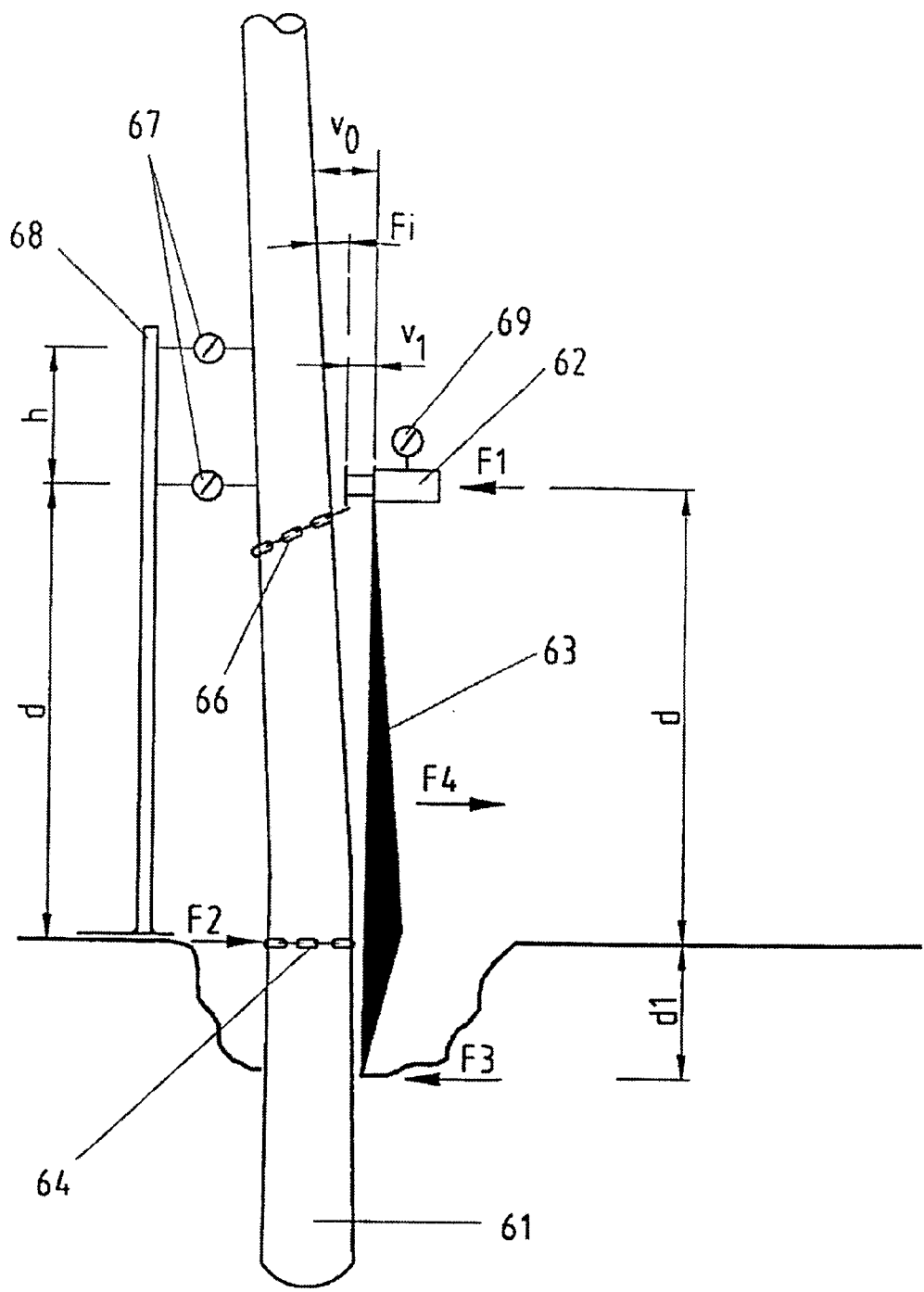

Referring to FIG. 6B, a pole 61 is simultaneously:

pushed with force F1 by means of a hydraulic ram 62 which at the same time, by its extension, pushes the top end of a loading element 63 away from the pole 11, and pulled with force F2 by means of a restraining chain 64 which is attached to the lower part of the loading element 63, and pushed with force F3 at the bottom end of the loading element 63 below the ground level, until a preset load F1 of-e.g. 10 kN is obtained on a load cell 65.

The loading element 63 can be operated manually or by suitable mechanical means such as a crane, hammer, or the like.

The loading element 63 may be additionally loaded with force F4 by suitable mechanical means such as a crane, hydraulic ram, or the like so that the pole 61 is bent at the ground level yet it does not move at its top and therefore there is no need of slackening or disconnecting of the wires attached to the pole top.

A chain 66 is attached to the head of the hydraulic ram 62 for safety purposes in case of the pole failure.

A reference base 68 may be fixed in the ground, or be mounted to the underground portion of the pole (for example below the bottom end of the loading element 63 where normally the pole does not move as forces F1, F2, and F3 balance each other), to provide a reference for a plurality of spaced displacement gauges 67 which are releasably attached to the pole 61.

The displacement of the pole is read off the displacement gauges 67 (for example dial gauges) and the residual strength of the pole is calculated by feeding the applied load and corresponding displacement into a programmed computer.

The apparatus shown in FIG. 6B can be portable, on its own wheels or operated by a truck mounted crane or the like.

Figure 6C:
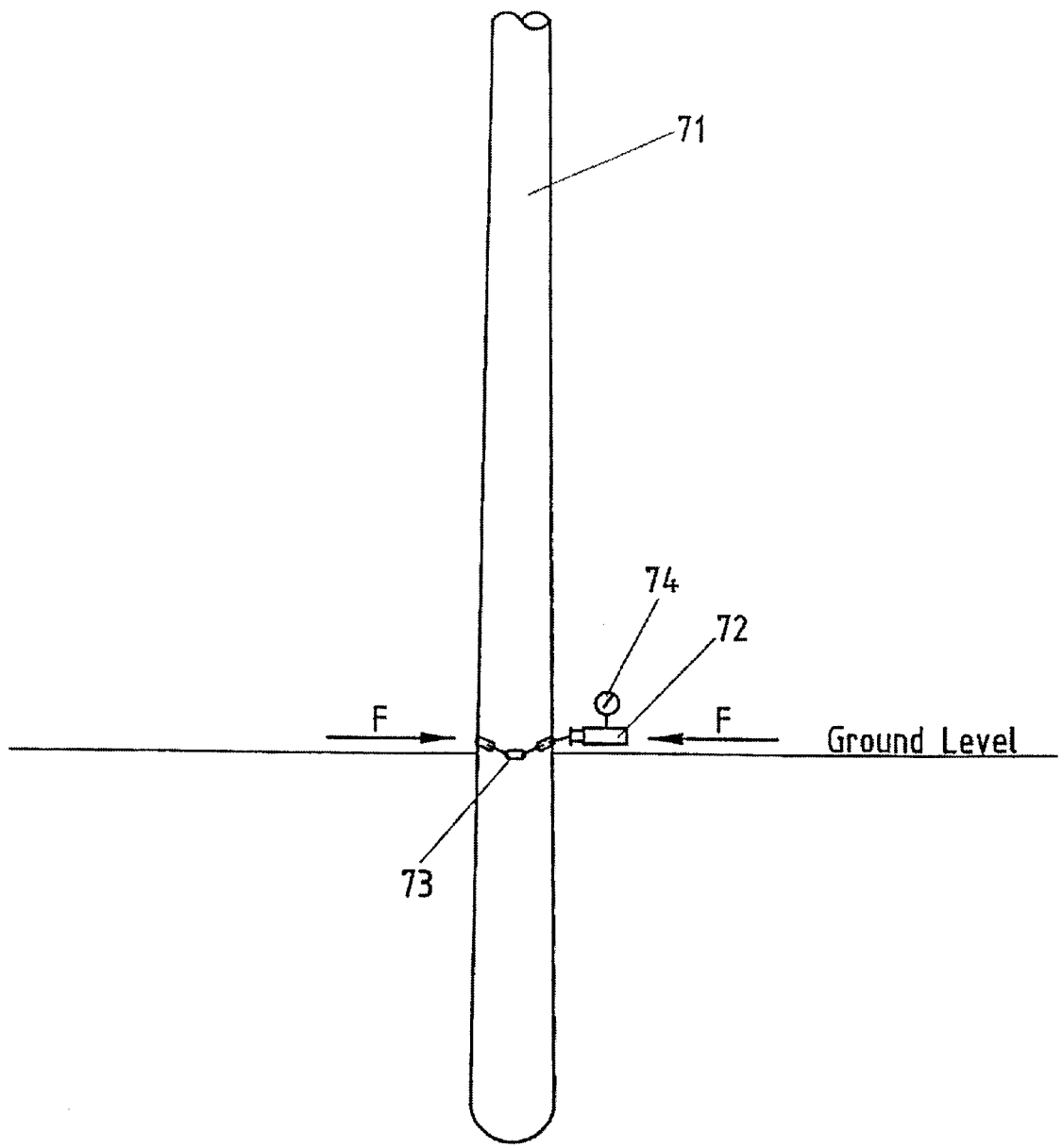

Referring to FIG. 6C, a pole 71 is simultaneously cut or squashed with two equal forces F by means of a hydraulic ram 72 and chain (or other suitable link) 73, connected to the hydraulic ram 72 and going around the pole 71, until a preset load F is obtained on a load cell 74.

The apparatus shown in FIG. 6C can be portable, on its own wheels or operated by a truck mounted crane or the like.

In all the embodiments illustrated in FIGS. 1 to 6C, the pole is tested under a Go/No Go situation. During the loading, both the pole and load cell readings are closely observed. If the pole fails, i.e. the pole cracks and load cell reading drops suddenly,.the pole is considered unsafe and sooner or later it must be either reinforced or replaced.

In the embodiment illustrated in FIG. 6B, the residual strength of the pole is measured by the displacement of the pole under a preset applied load of e.g. 10 kN. If the residual strength of the pole is calculated to be below a set threshold, the pole will be considered unserviceable.

The great value of the presented method resides in the fact that only one or few readings are required to check whether a pole has a required strength.

It will be readily apparent to the skilled addressee that the present invention provides simple, efficient and reliable means for checking the required strength of poles in a non-destructive manner (unless the pole's strength is below a preset safety level).

The claimed apparatus invention allows additionally for a quick test of poles which may have conductors attached from all directions or which may be embedded in a soft foundation.

Referring now to each of FIGS. 7 to 15, there is illustrated part of a pole support for ground poles and which can be driven into the ground next to the pole. Each pole support has a pair of spaced apart parallel longitudinal end plates 51, 52 interconnected approximately mid-way their ends by an intermediate plate 53. In the embodiment, the plates are formed from strong steel plates which may be welded together or formed integrally to form a strong rigid unit. End plates 51, 52 are spaced apart sufficiently to allow a pole to extend at least partially between the end plates, and/or to at least allow the end plates to contact and support the pole. Each of the end plates has a front longitudinal edge 54, 55 and a rear longitudinal edge 56, 57.

In each case, the front longitudinal edges 54, 55 constitute edges of the rectangular steel plate and are quite sharp, but as these edges are against the pole, there is little likelihood of any injury being caused to passers by.

Rear longitudinal edges 56, 57 extend rearwardly and can be contacted by passers by. These edges extend sufficiently from the pole to create a safety hazard as the end plate must be sufficiently wide to prevent the pole support from being or collapsing under the forces applied to it from the ground pole.

To prevent injury from occurring, the pole support includes means to reduce the sharp edge on each rear longitudinal edge 56, 57.

FIGS. 7A and 7B illustrate one embodiment whereby steel tubes are welded onto the edges (FIG. 7A) or inwardly from the edges (FIG. 7B) and where the tubes are sufficiently rounded to prevent injury from occurring.

FIG. 8 illustrates a version where the end plates are bent inwardly and steel tubes are welded to the longitudinal edges to improve the safety.

FIG. 9 shows an alternative where the tubes are slotted and can be pressed over the end plates, or where each tube is formed from two half sections which are attached to each side of the end plate and then welded or otherwise fixed together.

FIG. 10 shows a variation where a cover plate, typically formed from steel, extends across both rear longitudinal edges 16, 17 and where the cover plate has edges which are bent inwardly to contact the outer face of each end plate.

FIG. 11 shows a variation where a cover plate extends over the outside of each rear longitudinal edge and is attached thereto by spot welding or other suitable means, and where the cover plate has cut-out portions.

FIG. 12 illustrates another variation showing tubes welded or otherwise attached to the rear longitudinal edges.

Figure 13:
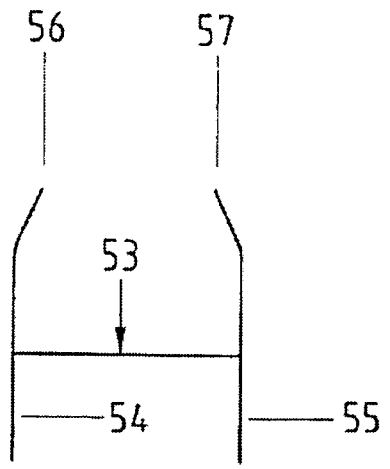
FIG. 13 illustrates a seventh embodiment of the invention.

FIG. 13 shows a variation where the end plates are bent inwardly to form a curve which provides a measure of safety.

Figure 14A:
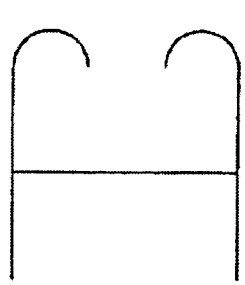
FIGS. 14A. and 14B illustrate variations of an eighth embodiment of the invention.
Figure 14B:
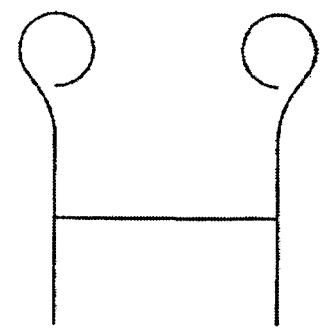

FIGS. 14A and 14B shows a more extreme alternative where the end plate is bent inwardly further such that the rear longitudinal edges now face the intermediate plate 53. In FIG. 14B, the end plate has a slightly more complicated profile.

Figure 15:
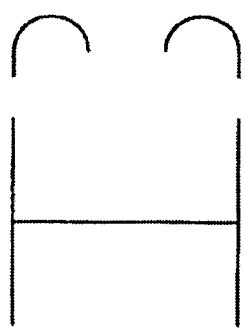
FIG. 15 illustrates a ninth embodiment of the invention.

FIG. 15 illustrates a variation where U-shaped steel plates are welded or otherwise attached onto each rear longitudinal edge 56, 57 rather than having to bend the end plates themselves.

The pole support, by having the particular profile of a pair of longitudinal end plates and an intermediate plate, provides a simple yet strong profile which can be hammered into the ground next to the pole. The profile ensures minimal displacement of earth and therefore minimal force required to hammer the support into the ground. The support has no enclosed profiles or cavities which can fill with moisture and cause corrosion of the support. The intermediate plate provides a transverse member which, when hammered into the ground, gives an excellent resistance to any force applied to it by the pole. The end plates provide excellent resistance to sideways movement, therefore the combination of the end plates and the intermediate plate provides excellent resistance against sideways movement as well as to and from movement.

It should be appreciated that various other changes and modifications may be made to the embodiments described without departing from the spirit and scope of the invention as claimed.

What is claimed is:

1. An apparatus for testing a pole having two opposed ends, the apparatus comprising:
   a. an elongate rigid beam having a first end and a second end and which is adapted to extend along the pole,
   b. an attachment member which is substantially inextensible and which extends at least partially about the pole to attach the beam to the pole intermediate the ends of the pole, and
   c. force means to apply a force to the beam to pull at least part of the beam away from the pole when the beam is attached to the pole.

2. The apparatus of claim 1, wherein the force means pulls one said end of the beam away from the pole.

3. The apparatus of claim 2, wherein the attachment member is adjacent a middle portion of the beam.

4. The apparatus of claim 3, wherein the attachment member is a chain.

5. The apparatus of claim 4, wherein the force means is a ram.

6. The apparatus of claim 5, wherein the pole is an in ground pole and the chain is attached to the pole and the beam adjacent the ground surface.

7. The apparatus of claim 6, wherein the said first end of the beam is below the ground surface and the said second end is above the ground surface.

8. The apparatus of claim 7, wherein one end of the ram is attached to the beam and the other end of the ram, in use, pushes against the pole.

9. The apparatus of claim 8, wherein operation of the ram causes the said second end of the beam to be pulled away from the pole, causes a pulling force on the pole where the attachment member is attached to the pole, and causes a pushing force to be applied to the pole at the first end of the beam.

10. The apparatus of claim 3, wherein the pole is an in ground pole and the chain is attached to the pole and the beam adjacent the ground level.

11. The apparatus of claim 10, wherein the lower end of the beam is below the ground surface.

12. The apparatus of claim 5, having a ram chain, one end of the ram being attached to the ram chain, the ram chain being attached to the one said end of the beam, and the other end of the ram pushing against the pole in use.

13. The apparatus of claim 12, wherein the pole is an in ground pole and the chain (15) attaches the beam to the pole below the ground surface.

14. The apparatus of claim 1, wherein the force means applies a force to the beam in relation to the pole adjacent a middle portion of the beam.

15. The apparatus of claim 14, wherein the attachment member is adjacent a middle portion of the beam.

16. The apparatus of claim 1, including a pole support adapted to be driven into the ground next to the pole, the support having a pair of spaced apart longitudinal end plates which are interconnected intermediate their ends by an intermediate plate to define a channel, the end plates being spaced apart to allow the ground pole to pass at least partially between the end plates and into the channel, each end plate having a front longitudinal edge which in use is adjacent the pole and a rear longitudinal edge which in use is directed away from the pole, the pole support having means to reduce a sharp edge on the rear longitudinal edge.

17. The apparatus of claim 16, wherein the spaced apart longitudinal end plates are substantially parallel to each other and are sufficiently long to allow them to be driven into the ground to a suitable distance while still providing sufficient length above the ground to provide support to the ground hole.

18. The apparatus of claim 17, having a length of 2 m to 5 m.

19. The apparatus of claim 18, wherein the end plates are spaced apart by a distance of between 15 to 50 cm, and the support is chosen to fit the pole such that there is a minimal gap between the end plate and the outer surface of the pole which could snag fingers of passers by or become a collection point for dirt and debris which may reduce the effective life of the pole.

20. The apparatus of claim 19, wherein the intermediate plate extends entirely along the length of the pole support by which is meant that the intermediate plates and the end plates are all of the same length.

21. The apparatus of claim 20, wherein the means to reduce the sharp edge is achieved by providing a curved portion on or adjacent the rear longitudinal edge of each end plate.

22. A method for testing a pole, the method comprising positioning an elongate rigid beam having a first end and a second end along the pole, attaching the beam to the pole by an attachment member which is substantially inextensible and which extends at least partially about the pole to attach the beam to the pole intermediate the ends of the pole, and applying a force means to apply a force to the beam to pull at least part of the beam away from the pole when the beam is attached to the pole.

23. The method of claim 22, including the steps of: calculating the minimum required strength of the pole and load to be applied to the pole equivalent to the minimum strength including any required safety factors, applying a preset load via the force means to the pole equivalent to the calculated minimum strength, and observing if the pole withstands the applied load without failure and so meets the minimum required strength.

24. The method of claim 22, including the steps of:

applying a preset load to the pole via the force means, measuring the displacement of the pole under the load, and from the applied load and the displacement, calculating the residual strength of the pole from predetermined formula (e), tabulated scales, or by a programmed calculator or computer.

25. The method of claim 22, including the steps of:

applying a load to the pole via the force means to cause the pole to undergo a preset displacement, measuring the load applied to the pole, and from the applied load and the displacement, calculating the residual strength of the pole from predetermined formula (e), tabulated scales, or by a programmed calculator or computer.

* * * * *